US012109126B1

(12) United States Patent
Gunther

(10) Patent No.: US 12,109,126 B1
(45) Date of Patent: Oct. 8, 2024

(54) ALIGNMENT GUIDE FOR HUMERAL OR FEMORAL STEM REPLACEMENT PROSTHESES

(71) Applicant: Shoulder Innovations, Inc., Ann Arbor, MI (US)

(72) Inventor: Stephen B. Gunther, Cloverdale, CA (US)

(73) Assignee: Shoulder Innovations, Inc., Grand Rapids, MI (US)

( * ) Notice: Subject to any disclaimer, the term of this patent is extended or adjusted under 35 U.S.C. 154(b) by 253 days.

(21) Appl. No.: 16/701,118

(22) Filed: Dec. 2, 2019

Related U.S. Application Data

(63) Continuation of application No. 14/845,136, filed on Sep. 3, 2015, now Pat. No. 10,492,926.

(60) Provisional application No. 62/046,084, filed on Sep. 4, 2014.

(51) Int. Cl.
*A61F 2/46* (2006.01)
(52) U.S. Cl.
CPC .......... *A61F 2/4607* (2013.01); *A61F 2/4612* (2013.01); *A61F 2002/4625* (2013.01); *A61F 2230/0006* (2013.01); *A61F 2230/0067* (2013.01)
(58) Field of Classification Search
CPC ............. A61B 17/1684; A61B 17/1778; A61F 2/40–4081; A61F 2002/4007–4096
See application file for complete search history.

(56) References Cited

U.S. PATENT DOCUMENTS

| | | | |
|---|---|---|---|
| 2,781,758 A | 2/1957 | Jacques | |
| 3,979,778 A | 9/1976 | Stroot | |
| 4,003,095 A | 1/1977 | Gristina | |
| 4,012,796 A * | 3/1977 | Weisman | ............ A61F 2/30728 623/23.28 |
| 4,045,826 A | 9/1977 | Stroot | |
| 4,206,517 A | 6/1980 | Pappas et al. | |
| 4,261,062 A | 4/1981 | Amstutz et al. | |
| 4,404,693 A | 9/1983 | Zweymuller | |
| 4,550,450 A | 11/1985 | Kinnett | |
| 4,698,063 A * | 10/1987 | Link | ................... A61F 2/30739 623/23.22 |

(Continued)

FOREIGN PATENT DOCUMENTS

| | | |
|---|---|---|
| AU | 2018251815 | 3/2024 |
| DE | 4220217 | 12/1993 |

(Continued)

OTHER PUBLICATIONS

U.S. Appl. No. 16/701,118, filed Dec. 2, 2019, Gunther.

(Continued)

*Primary Examiner* — Matthew J Lawson
(74) *Attorney, Agent, or Firm* — Knobbe, Martens, Olson & Bear, LLP

(57) ABSTRACT

The disclosure herein provides methods, systems, and devices for assisting alignment of humeral or femoral stems during replacement surgery. In one illustrative embodiment, a slotted disk is configured to position a prosthetic stem into a canal in the humerus when the stem is driven through the slot. In another illustrative embodiment, a similar slotted disk structure is configured to position a prosthetic stem into a canal in the femur.

10 Claims, 7 Drawing Sheets

(56) References Cited

U.S. PATENT DOCUMENTS

| | | | |
|---|---|---|---|
| 4,700,660 A * | 10/1987 | Levchenko | C23C 14/243 |
| | | | 118/726 |
| 4,783,192 A * | 11/1988 | Wroblewski | A61F 2/30728 |
| | | | 623/23.21 |
| 4,827,919 A * | 5/1989 | Barbarito | A61F 2/30724 |
| | | | 606/86 R |
| 4,865,605 A | 9/1989 | Dines et al. | |
| 4,908,036 A * | 3/1990 | Link | A61F 2/30728 |
| | | | 623/23.22 |
| 4,964,865 A | 10/1990 | Burkhead et al. | |
| 4,986,833 A | 1/1991 | Worland | |
| 4,990,161 A | 2/1991 | Kampner | |
| 5,030,219 A | 7/1991 | Matsen, III et al. | |
| 5,032,132 A | 7/1991 | Matsen, III et al. | |
| 5,080,673 A | 1/1992 | Burkhead et al. | |
| 5,108,440 A | 4/1992 | Grundei | |
| 5,281,226 A | 1/1994 | Davydov et al. | |
| 5,282,865 A | 2/1994 | Dong | |
| 5,314,479 A | 5/1994 | Rockwood, Jr. et al. | |
| 5,314,489 A | 5/1994 | Hoffman et al. | |
| 5,344,458 A | 9/1994 | Bonutti | |
| 5,358,525 A | 10/1994 | Fox et al. | |
| 5,370,694 A | 12/1994 | Davidson | |
| 5,437,677 A | 8/1995 | Shearer et al. | |
| 5,462,563 A | 10/1995 | Shearer et al. | |
| 5,480,450 A * | 1/1996 | James | A61B 17/8808 |
| | | | 606/92 |
| 5,489,309 A | 2/1996 | Lackey et al. | |
| 5,489,310 A | 2/1996 | Mikhail | |
| 5,507,748 A * | 4/1996 | Sheehan | A61B 17/8808 |
| | | | 606/92 |
| 5,507,819 A | 4/1996 | Wolf | |
| 5,514,184 A | 5/1996 | Doi | |
| 5,549,683 A | 8/1996 | Bonutti | |
| 5,593,448 A | 1/1997 | Dong | |
| 5,702,447 A | 12/1997 | Walch et al. | |
| 5,702,486 A | 12/1997 | Craig et al. | |
| 5,746,771 A * | 5/1998 | Clement, Jr. | A61F 2/4684 |
| | | | 623/23.22 |
| 5,755,811 A | 5/1998 | Tanamal et al. | |
| 5,769,856 A | 6/1998 | Dong et al. | |
| 5,800,551 A | 9/1998 | Williamson et al. | |
| 5,928,285 A | 7/1999 | Bigliani et al. | |
| 6,019,766 A * | 2/2000 | Ling | A61F 2/4609 |
| | | | 606/86 R |
| 6,037,724 A | 3/2000 | Buss et al. | |
| 6,228,119 B1 | 5/2001 | Ondria et al. | |
| 6,231,913 B1 | 5/2001 | Schwimmer et al. | |
| 6,290,726 B1 | 9/2001 | Pope et al. | |
| 6,334,874 B1 | 1/2002 | Tornier et al. | |
| 6,364,910 B1 | 4/2002 | Shultz et al. | |
| 6,368,353 B1 | 4/2002 | Arcand | |
| 6,379,386 B1 | 4/2002 | Resch et al. | |
| 6,458,136 B1 | 10/2002 | Allard et al. | |
| 6,514,287 B2 | 2/2003 | Ondria et al. | |
| 6,520,964 B2 | 2/2003 | Tallarida et al. | |
| 6,589,281 B2 | 7/2003 | Hyde, Jr. | |
| 6,610,067 B2 | 8/2003 | Tallarida et al. | |
| 6,620,197 B2 | 9/2003 | Maroney | |
| 6,673,115 B2 | 1/2004 | Resch et al. | |
| 6,679,916 B1 | 1/2004 | Frankle et al. | |
| 6,679,917 B2 | 1/2004 | Ek | |
| 6,699,289 B2 | 3/2004 | Lannotti et al. | |
| 6,709,463 B1 | 3/2004 | Pope et al. | |
| 6,712,823 B2 | 3/2004 | Grusin et al. | |
| 6,761,740 B2 | 7/2004 | Tornier | |
| 6,783,549 B1 | 8/2004 | Stone et al. | |
| 6,875,234 B2 | 4/2005 | Lipman et al. | |
| 6,953,478 B2 | 10/2005 | Bouttens et al. | |
| 7,011,686 B2 | 3/2006 | Ball et al. | |
| 7,044,973 B2 | 5/2006 | Rockwood et al. | |
| 7,238,089 B2 | 7/2007 | Tsumuraya et al. | |
| 7,238,208 B2 | 7/2007 | Camino et al. | |
| 7,261,741 B2 * | 8/2007 | Weissman | A61L 27/58 |
| | | | 623/23.22 |
| 7,294,149 B2 | 11/2007 | Hozack et al. | |
| 7,320,709 B2 | 1/2008 | Felt et al. | |
| 7,329,284 B2 | 2/2008 | Maroney et al. | |
| 7,465,319 B2 | 12/2008 | Tornier | |
| 7,517,364 B2 | 4/2009 | Long et al. | |
| 7,618,462 B2 | 11/2009 | Ek | |
| 7,678,151 B2 | 3/2010 | Ek | |
| 7,749,278 B2 | 7/2010 | Frederick et al. | |
| 7,753,959 B2 | 7/2010 | Berelsman et al. | |
| 7,766,969 B2 | 8/2010 | Justin et al. | |
| 7,776,098 B2 | 8/2010 | Murphy | |
| 7,892,287 B2 | 2/2011 | Deffenbaugh | |
| 7,922,769 B2 | 4/2011 | Deffenbaugh et al. | |
| 8,007,538 B2 | 8/2011 | Gunther | |
| 8,038,719 B2 | 10/2011 | Gunther | |
| 8,048,161 B2 | 11/2011 | Guederian et al. | |
| 8,048,167 B2 | 11/2011 | Dietz et al. | |
| 8,303,665 B2 | 11/2012 | Tornier et al. | |
| 8,529,629 B2 | 9/2013 | Angibaud et al. | |
| 8,608,805 B2 | 12/2013 | Forrer et al. | |
| 8,721,726 B2 | 5/2014 | Capon et al. | |
| 8,778,028 B2 | 7/2014 | Gunther et al. | |
| 8,840,671 B2 | 9/2014 | Ambacher | |
| 8,920,508 B2 | 12/2014 | Lannotti et al. | |
| 8,940,054 B2 | 1/2015 | Wiley et al. | |
| 9,114,017 B2 | 8/2015 | Lappin | |
| 9,283,083 B2 | 3/2016 | Winslow et al. | |
| 9,381,086 B2 | 7/2016 | Ries et al. | |
| 9,545,311 B2 | 1/2017 | Courtney, Jr. et al. | |
| 9,545,312 B2 | 1/2017 | Tornier et al. | |
| 9,610,166 B2 | 4/2017 | Gunther et al. | |
| 9,615,839 B2 | 4/2017 | Olson | |
| 9,693,784 B2 | 7/2017 | Gunther | |
| 9,867,710 B2 | 1/2018 | Dalla Pria et al. | |
| 9,962,265 B2 | 5/2018 | Ek et al. | |
| 10,034,753 B2 * | 7/2018 | Dressler | A61B 17/1668 |
| 10,143,559 B2 | 12/2018 | Ries et al. | |
| 10,357,373 B2 | 7/2019 | Gargac et al. | |
| 10,492,926 B1 | 12/2019 | Gunther | |
| 10,702,390 B2 | 7/2020 | Chavarria et al. | |
| 10,779,952 B2 | 9/2020 | Gunther et al. | |
| 10,786,265 B2 | 9/2020 | Gunther | |
| 11,065,125 B2 | 7/2021 | Ball | |
| D977,643 S | 2/2023 | Ball et al. | |
| 11,696,772 B2 | 7/2023 | Gunther | |
| 11,771,561 B2 | 10/2023 | Running et al. | |
| 2001/0011192 A1 | 8/2001 | Ondria et al. | |
| 2001/0037153 A1 | 11/2001 | Rockwood, Jr. et al. | |
| 2001/0047210 A1 | 11/2001 | Wolf | |
| 2002/0055783 A1 | 5/2002 | Tallarida et al. | |
| 2002/0082702 A1 | 6/2002 | Resch et al. | |
| 2002/0087213 A1 | 7/2002 | Bertram, III | |
| 2002/0095214 A1 | 7/2002 | Hyde, Jr. | |
| 2002/0111689 A1 | 8/2002 | Hyde, Jr. et al. | |
| 2002/0138148 A1 | 9/2002 | Hyde, Jr. et al. | |
| 2003/0033019 A1 | 2/2003 | Lob | |
| 2003/0100952 A1 | 5/2003 | Rockwood, Jr. et al. | |
| 2003/0114933 A1 | 6/2003 | Bouttens et al. | |
| 2003/0125809 A1 | 7/2003 | Lannotti et al. | |
| 2003/0144738 A1 | 7/2003 | Rogalski | |
| 2003/0158605 A1 | 8/2003 | Tournier | |
| 2003/0163202 A1 | 8/2003 | Lakin | |
| 2003/0236572 A1 | 12/2003 | Bertram, III | |
| 2004/0002766 A1 | 1/2004 | Hunter et al. | |
| 2004/0039449 A1 | 2/2004 | Tournier | |
| 2004/0039451 A1 | 2/2004 | Southworth | |
| 2004/0059424 A1 | 3/2004 | Guederian et al. | |
| 2004/0064187 A1 | 4/2004 | Ball et al. | |
| 2004/0064189 A1 | 4/2004 | Maroney et al. | |
| 2004/0064190 A1 | 4/2004 | Ball et al. | |
| 2004/0107002 A1 | 6/2004 | Katsuya | |
| 2004/0122519 A1 | 6/2004 | Wiley et al. | |
| 2004/0122520 A1 | 6/2004 | Lipman et al. | |
| 2004/0167629 A1 | 8/2004 | Geremakis et al. | |
| 2004/0167630 A1 | 8/2004 | Rolston | |
| 2004/0193168 A1 | 9/2004 | Long et al. | |
| 2004/0193275 A1 | 9/2004 | Long et al. | |

(56) References Cited

U.S. PATENT DOCUMENTS

| | | |
|---|---|---|
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0199260 A1 | 10/2004 | Pope et al. |
| 2004/0220674 A1 | 11/2004 | Pria |
| 2004/0230311 A1 | 11/2004 | Cyprien et al. |
| 2004/0260398 A1 | 12/2004 | Kelman |
| 2005/0043805 A1 | 2/2005 | Chudik |
| 2005/0049709 A1 | 3/2005 | Tornier |
| 2005/0065612 A1 | 3/2005 | Winslow |
| 2005/0075638 A1 | 4/2005 | Collazo |
| 2005/0107882 A1 | 5/2005 | Stone et al. |
| 2005/0119531 A1 | 6/2005 | Sharratt |
| 2005/0177241 A1 | 8/2005 | Angibaud et al. |
| 2005/0261775 A1 | 11/2005 | Baum et al. |
| 2005/0278030 A1 | 12/2005 | Tornier et al. |
| 2006/0036328 A1 | 2/2006 | Parrott et al. |
| 2006/0069443 A1 | 3/2006 | Deffenbaugh et al. |
| 2006/0069444 A1 | 3/2006 | Deffenbaugh et al. |
| 2006/0069445 A1 | 3/2006 | Ondrla et al. |
| 2006/0200249 A1 | 9/2006 | Beguin et al. |
| 2007/0038302 A1 | 2/2007 | Shultz et al. |
| 2007/0050042 A1 | 3/2007 | Dietz et al. |
| 2007/0055380 A1 | 3/2007 | Berelsman et al. |
| 2007/0112433 A1 | 5/2007 | Frederick et al. |
| 2007/0118229 A1 | 5/2007 | Bergin et al. |
| 2007/0156246 A1 | 7/2007 | Meswania et al. |
| 2007/0179624 A1 | 8/2007 | Stone et al. |
| 2007/0225817 A1 | 9/2007 | Ruebelt et al. |
| 2007/0225818 A1 | 9/2007 | Reubelt et al. |
| 2008/0021564 A1 | 1/2008 | Gunther |
| 2008/0082175 A1* | 4/2008 | Holovacs ............... A61F 2/46 623/23.12 |
| 2008/0177327 A1 | 7/2008 | Malandain et al. |
| 2008/0234820 A1 | 9/2008 | Felt et al. |
| 2008/0294268 A1 | 11/2008 | Baum et al. |
| 2009/0105837 A1 | 4/2009 | LaFosse et al. |
| 2009/0125113 A1 | 5/2009 | Guederian et al. |
| 2009/0228112 A1 | 9/2009 | Clark et al. |
| 2009/0270866 A1 | 10/2009 | Poncet |
| 2009/0281630 A1 | 11/2009 | Delince et al. |
| 2009/0287309 A1 | 11/2009 | Walch et al. |
| 2010/0087876 A1 | 4/2010 | Gunther |
| 2010/0087877 A1 | 4/2010 | Gunther |
| 2010/0114326 A1 | 5/2010 | Winslow et al. |
| 2010/0161066 A1 | 6/2010 | Lonetti et al. |
| 2010/0217399 A1 | 8/2010 | Groh |
| 2010/0274360 A1 | 10/2010 | Gunther |
| 2011/0029089 A1 | 2/2011 | Giuliani et al. |
| 2011/0106266 A1 | 5/2011 | Schwyzer et al. |
| 2011/0137424 A1 | 6/2011 | Lappin et al. |
| 2011/0144758 A1 | 6/2011 | Deffenbaugh |
| 2011/0276144 A1 | 11/2011 | Wirth et al. |
| 2011/0313533 A1 | 12/2011 | Gunther |
| 2012/0209392 A1 | 8/2012 | Angibuad et al. |
| 2012/0239156 A1 | 9/2012 | De Wilde et al. |
| 2013/0150972 A1 | 1/2013 | Lannotti et al. |
| 2013/0060346 A1 | 3/2013 | Collins |
| 2013/0090736 A1 | 4/2013 | Katrana et al. |
| 2013/0150974 A1 | 6/2013 | Lannotti et al. |
| 2013/0194353 A1 | 8/2013 | Hirai et al. |
| 2013/0197651 A1 | 8/2013 | McDaniel et al. |
| 2013/0261752 A1 | 10/2013 | Lappin et al. |
| 2014/0025173 A1 | 1/2014 | Cardon et al. |
| 2014/0107794 A1 | 4/2014 | Deffenbaugh et al. |
| 2014/0253641 A1 | 9/2014 | Furuya |
| 2014/0257499 A1 | 9/2014 | Winslow et al. |
| 2015/0223941 A1 | 8/2015 | Lang |
| 2015/0265411 A1 | 9/2015 | Deransart et al. |
| 2016/0045323 A1 | 2/2016 | Kovacs et al. |
| 2016/0302934 A1 | 10/2016 | Chavarria et al. |
| 2017/0000617 A1 | 1/2017 | Ries et al. |
| 2017/0071749 A1 | 3/2017 | Lappin et al. |
| 2017/0202674 A1 | 7/2017 | Gunther et al. |
| 2017/0209275 A1* | 7/2017 | Levy ............... A61F 2/30724 |
| 2017/0360456 A1 | 12/2017 | Gunther |
| 2018/0071104 A1 | 3/2018 | Kovacs et al. |
| 2018/0078377 A1 | 3/2018 | Gargac et al. |
| 2021/0038401 A1 | 2/2021 | Ball et al. |
| 2021/0137693 A1 | 5/2021 | Ball et al. |
| 2021/0236292 A1 | 8/2021 | Chavarria et al. |
| 2021/0244547 A1 | 8/2021 | Gunther et al. |
| 2021/0251640 A1 | 8/2021 | Gunther |
| 2021/0338446 A1 | 11/2021 | Ball |
| 2022/0151795 A1 | 5/2022 | Running et al. |
| 2022/0175543 A1 | 6/2022 | Ball |
| 2022/0175544 A1 | 6/2022 | Ball et al. |
| 2023/0078024 A1 | 3/2023 | Gunther et al. |
| 2023/0080207 A1 | 3/2023 | Gunther et al. |

FOREIGN PATENT DOCUMENTS

| | | |
|---|---|---|
| DE | 10164328 A1 | 7/2003 |
| EP | 0299889 A2 | 1/1989 |
| EP | 0339530 A2 | 11/1989 |
| EP | 0570816 A1 | 11/1993 |
| EP | 1464305 A1 | 10/2004 |
| EP | 1858453 | 11/2007 |
| EP | 1952788 A1 | 8/2008 |
| EP | 2601912 | 6/2013 |
| EP | 2083759 B1 | 9/2015 |
| FR | 2248820 A1 | 5/1975 |
| FR | 2567019 A1 | 1/1986 |
| FR | 2695313 A1 | 3/1994 |
| JP | 04-282149 A | 10/1992 |
| JP | 2013-158909 | 8/2013 |
| JP | 2014-515651 | 7/2014 |
| WO | WO 2006/093763 | 8/2006 |
| WO | WO 2008/011078 | 1/2008 |
| WO | WO 2009/071940 | 6/2009 |
| WO | WO 2011/112425 | 9/2011 |
| WO | WO 2013/148437 | 10/2013 |
| WO | WO 2012/075183 | 4/2014 |
| WO | WO 2014/067961 | 5/2014 |
| WO | WO 2014/0195909 | 12/2014 |
| WO | WO 2018/181420 | 10/2018 |
| WO | WO 2019/178104 | 9/2019 |
| WO | WO 2019/213073 | 11/2019 |
| WO | WO 2020/185893 | 9/2020 |
| WO | WO 2023/183283 | 9/2023 |
| WO | WO 2024/026101 | 2/2024 |

OTHER PUBLICATIONS

U.S. Appl. No. 29/870,666, filed Feb. 1, 2023, Ball et al.
U.S. Appl. No. 18/349,805, filed Jul. 10, 2023, Gunther.
U.S. Appl. No. 18/477,416, filed Sep. 28, 2023, Running et al.
Biomet, "Absolute ™ Bi-Polar." 2001 in 2 pages.
Biomet, "Copeland" ™ Humeral Resurfacing Head, Interlok®/HA Coated Implant Information, 2003 in 1 page.
Biomet, "Copeland" ™ Humeral Resurfacing Head, 2001 in 12 pages.
Biomet, "Copeland™ Humeral Resurfacing Head, Surgical Technique," 2003 in 2 pages.
Boileau et al., "The Three-Dimensional Geometry of the Proximal Humerus. Implications for Surgical Technique and Prosthetic Design," J. Bone Joint Surg. Br. 79: 857-865, 1997.
Braun, et al., Modular Short-stem Prosthesis in Total Hip Arthroplasty: Implant Positioning and the Influence of Navigation, ORTHO SuperSite (Oct. 2007) in 8 pages.
Clavert et al. Glenoid resurfacing: what are the limits to asymmetric reaming for posterior erosion? J. Shoulder and Elbow Surg. Nov./Dec. 2007: 843-848.
Dalla Pria, Paolo. Slide presentation, entitled "Shoulder Prosthesis Design and Evolution", to the Naples International Shoulder Congress in Italy (2000) in 55 pages.
Depuy, "Global C.A.P., Surgical Technique Resurfacing Humeral Head Implant," 2004 in 23 pages.
Inset Mini-glenoid Brochure, Titan Modular Shoulder System Brochure, Ascension Orthopedics, 2011, 4 pages.

(56) References Cited

OTHER PUBLICATIONS

Karduna et al. Glenhumeral Joint Translations before and after Total Shoulder Arthroplasty. J. Bone and Joint Surg. 79(8) (1997): 1166-1174.

Levy et al., "Cementless Surface Replacement Arthroplasty of the Should. 5- to 10-year Results with the Copeland Mark-2 Prosthesis," J. Bone Joint Surg. Br. 83: 213-221, 2001.

Lima-Lto Medical Systems Glenoidi/Glenoids catalogue (2001) in 1 page.

Lima-Lto Miniglenoide Cementata document 7560.50.030 (1999) in 1 page.

Panisello, et al., Bone remodelling after total hip arthroplasty using an uncemented anatomic femoral stem: a three-year prospective study using bone densitometry, J Ortho Surg 14(1):32-37 (2006).

Ross, Mark and Duke, Phillip, "Early Experience In The Use of a New Glenoid Resurfacing Technique" Glenoid Presentation, SESA Nov. 4, 2006, Session 4/0800-0930 p. 93 in 1 page.

Tight Fit Tools, Right Angle Drill Attachment, Serial No. 00400 www.tightfittools.com/riganat.html in 1 page/downloaded Mar. 11, 2005.

TITAN(™) Modular Shoulder System Brochure, 2011, available at http://www.ascensionortho.com/Assets/PDF/TitanModular/TITANModularShoulder_Brochure-revD.pdf (2 pages).

Tournier et al., Enhancement of Glenoid Prosthesis Anchorage using Burying Technique. Techniques in Shoulder & Elbow Surgery 9(1)(2008): 35-42.

Wang et al., Biomechanical Evaluation of a Novel Glenoid Design in Total Shoulder Arthroplasty. J. Shoulder & Elbow Surgery (2005) 15: 129S-140S.

Biomet, "Copeland™ Humeral Resurfacing Head, Macrobond™ Implant Information," 2003 in 1 page.

Redacted letter from a third party dated Aug. 24, 2012 in 2 pages.

Statement of Grounds and Particulars of Opposition for Australian Patent Application No. 2006218936 dated Oct. 5, 2012 in 8 pages.

\* cited by examiner

ALIGNMENT GUIDE FOR HUMERAL OR FEMORAL STEM REPLACEMENT PROSTHESES

REFERENCE TO RELATED APPLICATIONS

This application claims the benefit under 35 U.S.C. § 119(e) as a nonprovisional application of U.S. Prov. App. No. 62/046,084 filed on Sep. 4, 2014, which is hereby incorporated by reference in its entirety.

BACKGROUND

Field of the Invention

The present invention relates, in some aspects, to the field of stem replacement prosthesis, and in particular, systems for positioning humeral and femoral implants.

Description of the Related Art

In certain cases, when a natural shoulder joint has degenerated as a result of disease, trauma, or other reasons, it may become desirable to replace parts of the natural shoulder joint with prosthetics. Conventional methods for shoulder replacement include replacing the head of the humerus with components that mimic the natural anatomy.

In particular, replacement of the humeral head with prosthetics presents surgical challenges. Typically, the surgery would include at least the following simplified steps. The surgeon first dislocates the natural humeral head from its ordinary position by rotating and extending the humerus. The surgeon then drills a hole through the humeral head into the medullary canal, removes the natural humeral head, and installs a prosthetic implant.

Typically the prosthetic humeral implant has at least two major components: a ball structure that replaces the humeral head and a stem structure that extends through a drilled hole into the medullary canal of the humerus. The stem is used to fix the prosthetic humeral head in place and provide stability.

One challenge to the surgery is positioning the stem through the cut surface of the humerus into the center of the canal. Inaccuracy at this step can lead to anterior or posterior angulation, which can result in a misaligned prosthetic stem or head. The repercussions of such misalignment can be problematic for the patient. Besides possible injury sustained during the implantation itself, a misaligned prosthetic stem and/or head predisposes the patient to a loosened stem, shoulder joint instability, and/or altered shoulder joint biomechanics. These issues can cause stiffness, discomfort, and early surface wear. In some cases, the patient will require undesirable revision shoulder arthroplasty, humeral stem removal, and/or other procedures.

A similar procedure, with similar challenges, is involved with hip replacement. Procedures, including total hip replacement or hemiarthroplasty, replace parts of the hip joint with prosthetics. In these procedures, the femoral head may be replaced with a prosthetic. Similar to the humeral implantation described above, a femoral implant might include at least a head and a stem. The stem extends into the femur, thereby stabilizing the prosthetic. The prosthetic femoral structure mimics the natural femur.

SUMMARY

The systems, methods, and devices described herein have innovative aspects, no single one of which is indispensable or solely responsible for their desirable attributes. Without limiting the scope of the claims, some of the advantageous features will now be summarized.

One aspect of the present invention is the realization that conventional systems for prosthetic replacement of the shoulder joint require additional care to prevent misalignment of prosthetic humeral implants. Thus, there exists a need for improved systems, methods, and devices for aligning prosthetic humeral heads and stems during surgery.

One non-limiting embodiment of the present invention includes an alignment guide, such as a slotted disk or other structure to guide a prosthetic stem into the medullary canal of the humerus during shoulder replacement surgery. In some embodiments, a prosthetic stem kit includes a prosthetic stem (e.g., a humeral or femoral stem) and an alignment guide as disclosed, for example herein.

In some embodiments, the dimensions of the disk are configured to fit the surface of a surgical bone cut after the natural humeral head has been removed. The slotted disk may have a slot that is an integral part of the disk or one that is separately attachable. In some embodiments, the disk can stably sit at a 90 degree angle to the longitudinal axis of the bone cut. In other embodiments, the disk can sit at an angle other than 90 degrees to the longitudinal axis of the bone cut to match an angle desirable for proper prosthetic stem and head alignment.

In some embodiments, the slot may also be configured to the dimensions and/or geometry of the prosthetic stem. The slot may also have curves to match the curves of the prosthetic stem. In some embodiments, the slot can sit at a 90 degree angle to the disk. In other embodiments, the slot can sit at an angle other than 90 degrees to match an angle desirable for proper prosthetic stem and head alignment.

In another non-limiting embodiment, the surgeon performs the method of positioning the slotted disk at the end of a humerus after the natural humeral head has been removed. The surgeon then slides the prosthetic stem through the slotted disk for proper stem alignment. In some embodiments the prosthetic head may be attached to the prosthetic stem after the prosthetic stem has been implanted. In other embodiments, the prosthetic stem and prosthetic head are implanted as an attached unit.

In another non-limiting embodiment, the slotted disk is removed at some point during surgery.

In another non-limiting embodiment, a slotted disk structure, as described in the embodiments above, is used for guiding a prosthetic stem into a femur. The stem can be used as part of femoral prosthesis.

BRIEF DESCRIPTION OF THE DRAWINGS

The drawings are provided to illustrate example embodiments described herein and are not intended to limit the scope of the disclosure.

DETAILED DESCRIPTION

Figure 1:
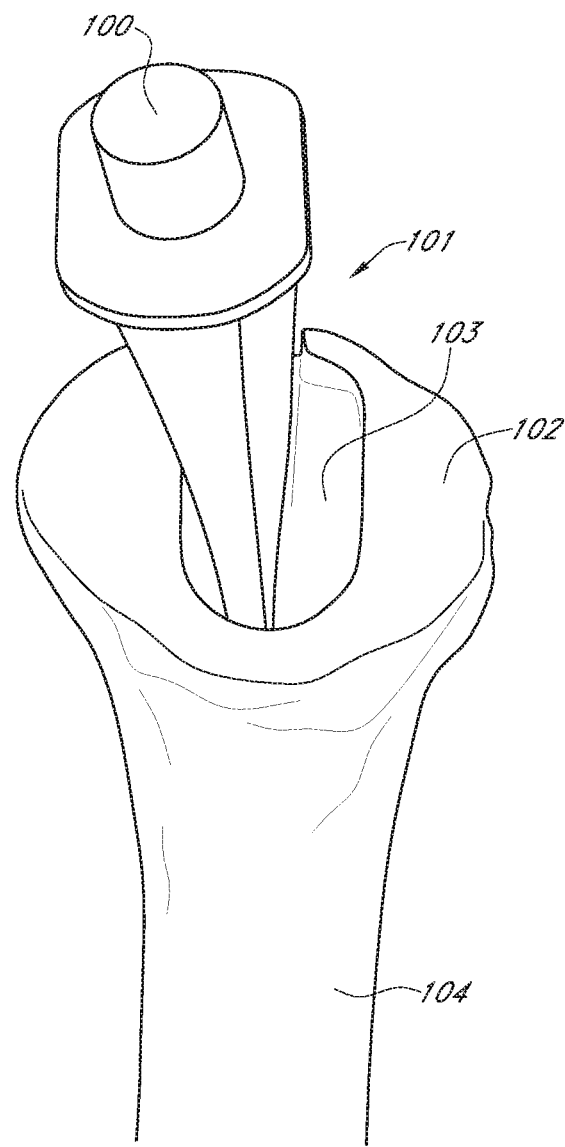
FIG. 1 is an image showing an example of a misaligned prosthetic stem.

FIG. 1 shows a misaligned prosthetic stem 101. 102 is a bone cut surface after a natural humeral head has been removed. Stem 101 is inserted through bone cut surface 102 into the surgically created path 103, which leads into the medullary canal located inside humerus bone 104. In some embodiments, prosthetic stems that can be used or modified for use with alignment guides as disclosed herein can be found, for example, in U.S. Pub. No. 2012/0172996 A1 to Ries et al., which is hereby incorporated by reference in its entirety.

Figure 2:
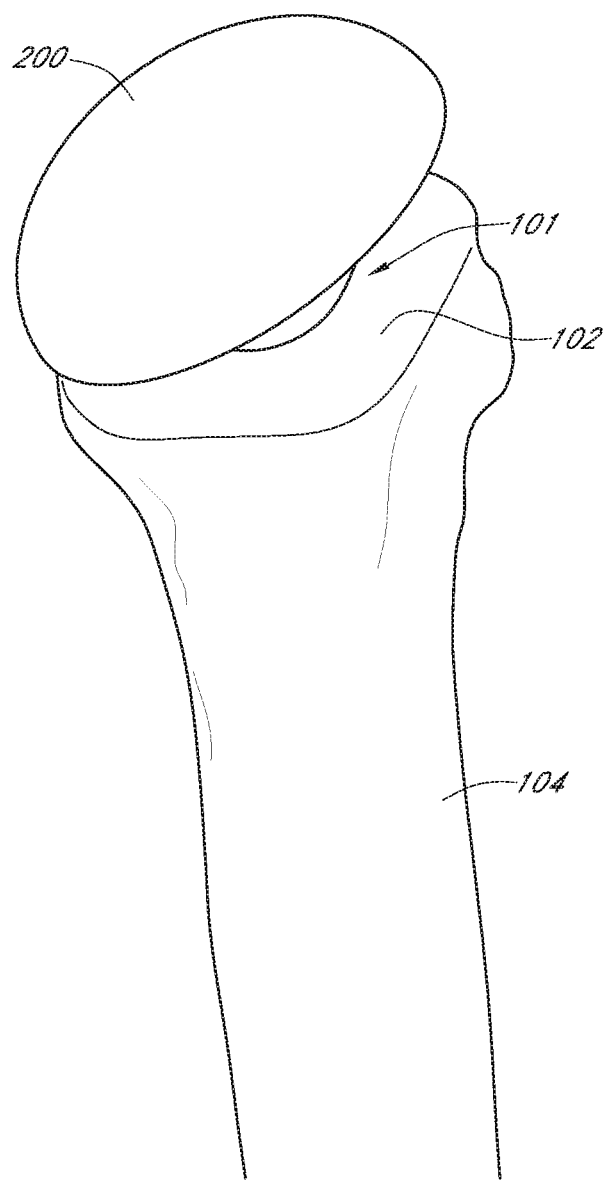
FIG. 2 is an image showing an example of misalignment of a prosthetic humeral head because of a misaligned stem.

In general, stem misalignment occurs when a stem is not properly positioned into the humerus. Some examples of this kind of misalignment might include at least the following: implanting the stem at an angle, rotating the stem, and/or positioning the stem in a way that does not match the geometry of the medullary canal or the surgical path to it. Current procedures are susceptible to such misalignment due to the difficulty in positioning the stem. As FIG. 1 demonstrates, the lack of visibility of the canal in element 104, and the geometry of the canal itself, can make it difficult for a surgeon to know if the stem is properly angled while implanting a stem during surgery. And even if positioning is slightly off, it can cause additional problems for the patient. A misaligned stem can lead to a misaligned prosthetic humeral head, as shown in FIG. 2. Head 200 attaches to stem 101 using element 100. As such, misaligned stem 101 causes prosthetic head 200 to not be flush against bone cut surface 102.

As mentioned above, a misaligned humeral head and/or stem predisposes a patient to a loosened stem, shoulder joint instability, and/or altered shoulder joint biomechanics, any of which can lead to discomfort and eventually require additional surgical procedures. Embodiments of alignment guides and methods of use as disclosed herein can assist in providing proper rotational and/or anterior-posterior alignment of the implanted stem. In some embodiments, the alignment guides and methods of use can assist in reliably providing rotational and/or anterior-posterior alignment within about 10%, or within about 5% of optimal. In some embodiments, the alignment guides can allow for prosthetic heads to be flush, that is, substantially level to or even with the plane of the bone cut surface.

Figure 3:
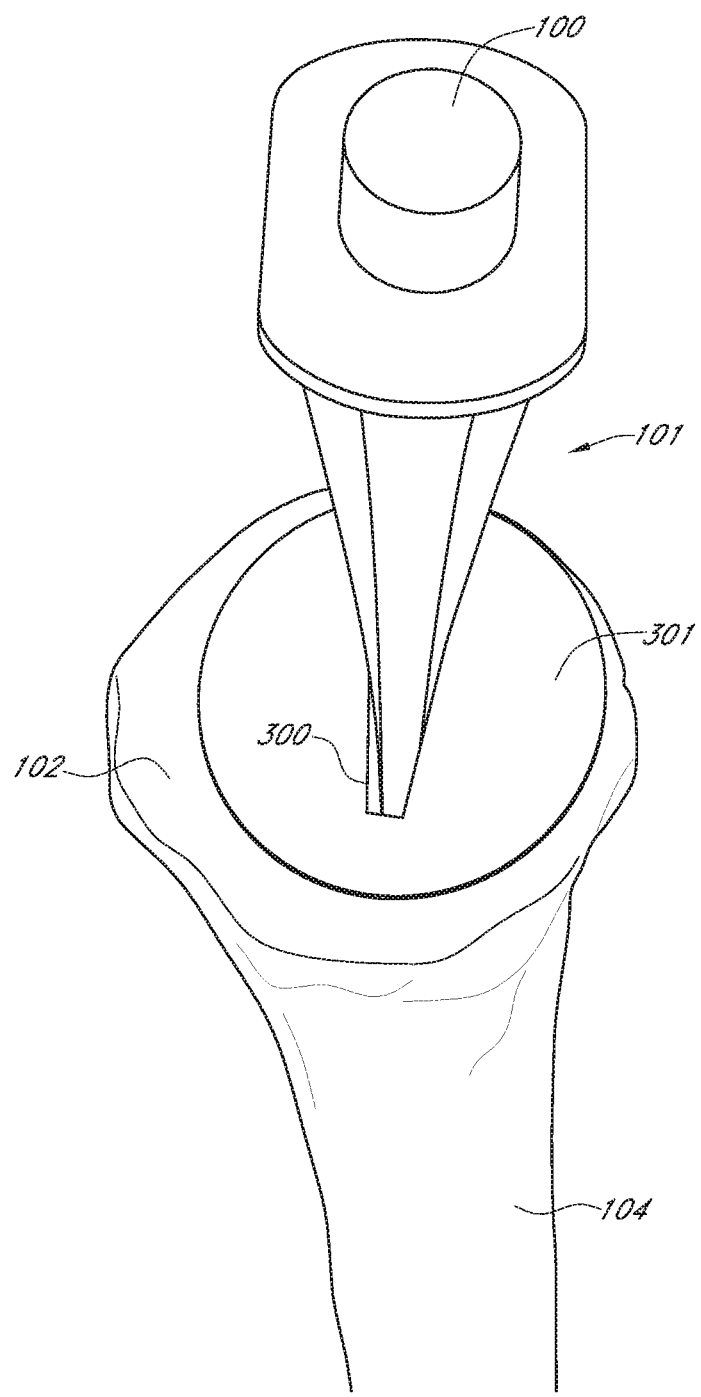
FIG. 3 and FIG. 4 are images showing an example of a slotted disk used to properly align a stem.
Figure 4:
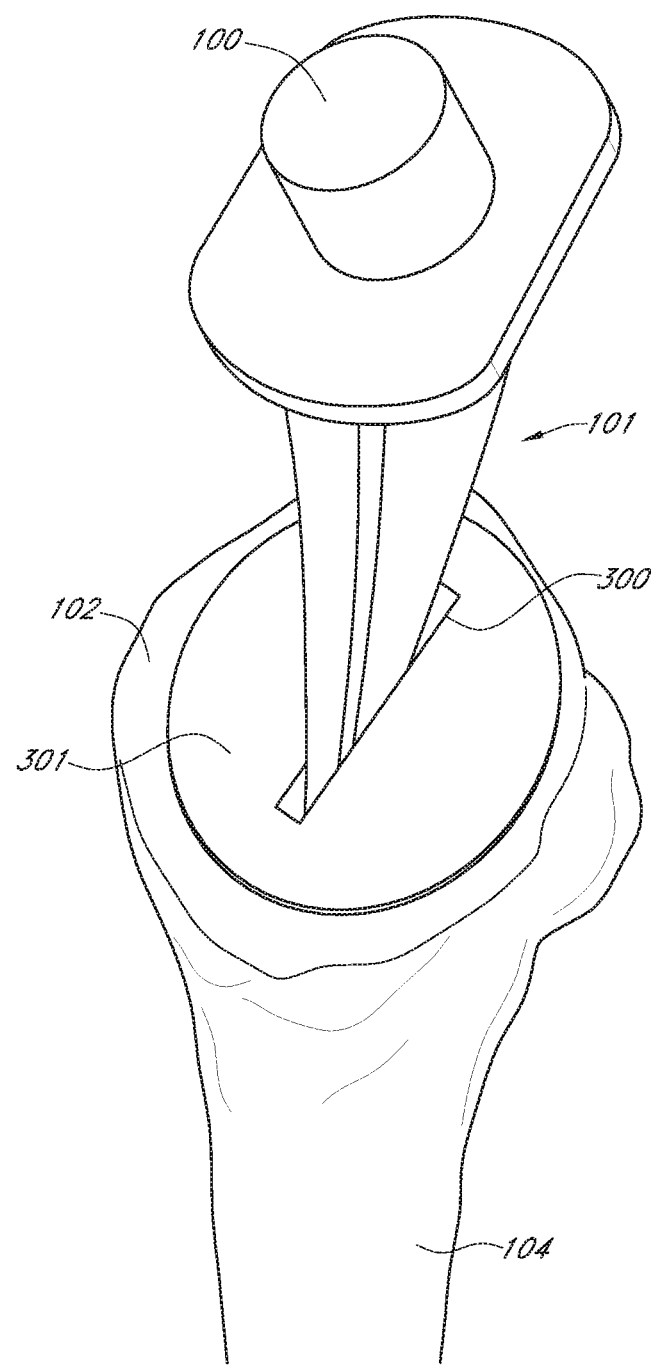

FIG. 3 and FIG. 4 illustrate some embodiments of the present invention. The images show a substantially flat slotted disk structure 301 with slot 300 in it. The alignment guide 301 could include no more than a single slot, or a plurality of slots in other embodiments. The disk structure 301 can have a first surface configured to be in contact with the bone cut surface 301, and a second surface opposite the first surface typically visualized by the physician. Disk 301 and slot 300 are configured to properly guide the stem 101 into a canal in humerus 104. The dimensions of disk 301 and slot 300 are also configured to fit the dimensions of the bone cut surface 102. In some embodiments, the slot has a surface area that is about, no more than about, or less than about 5%, 10%, 15%, 20%, 25%, 30%, 35%, 40%, 45%, 50%, 55%, 60%, 65%, 70%, or 75% relative to the surface area of the second surface of the disk 301. In some embodiments, the slot can be centered with respect to a diameter of the disk as illustrated, or offset in other embodiments. The slot 300 is shaped to receive a stem 101 as shown. In some embodiments, the slot 300 has a major axis dimension that is at least 2×, 3×, 4×, 5×, 6×, 7×, 8×, 9×, 10×, or more with respect to a minor axis dimension of the slot 300 perpendicular to the major axis dimension. In some embodiments for guiding a humeral stem, for example, the slot 300 can have a major axis dimension of between about 5 mm and about 30 mm, such as between about 10 mm and about 25 mm, or about 5 mm, 10 mm, 15 mm, 20 mm, 25 mm, or 30 mm, or ranges including any two of the aforementioned values for example. In some embodiments for guiding a femoral stem, for example, the slot 300 can have a major axis dimension of between about 30 mm and about 100 mm, such as between about 40 mm and about 75 mm, or about 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, or ranges including any two of the aforementioned values for example. In some embodiments, the slot 300 has a minor axis dimension of between about 2 mm and about 50 mm, such as between about 5 mm and about 20 mm, or about 2 mm, 3 mm, 4 mm, 5 mm, 10 mm, 15 mm, 20, mm, 25 mm, 30 mm, or ranges including any two of the aforementioned values for example. In some embodiments, the alignment guide 301 has a thickness of between about 2 mm and about 50 mm, between about 5 mm and about 25 mm, between about 5 mm and about 20 mm, or about or less than about 50 mm, 45 mm, 40 mm, 35 mm, 30 mm, 25 mm, 20 mm, 15 mm, 10 mm, 9 mm, 8 mm, 7 mm, 6 mm, 5 mm, 4 mm, 3 mm, 2 mm, 1 mm, or less. In some embodiments, the diameter, length, and/or width of the alignment guide 301 can include dimensional values or ranges described, for example, in this paragraph.

In some embodiments, the slot 300 can be shaped as a rectangle as shown, square, rhomboidal, triangular, arcuate (e.g., circular, oval, semilunar, etc.), or another desired shape. In some embodiments, the slot 300 could also be a channel, groove, or box-type slide structure having one or more walls defining an aperture for receiving the stem 101 therethrough and configured to guide the stem down properly to the metaphyseal bone surface such as into a recess formed into the bone. In some embodiments, one or more of the sidewalls defining the slot 300 can project axially either in an anterior and/or posterior direction in order to circumscribe the stem 101 along a longer length of the stem 101, such that the length dimension of one or more of the sidewalls of the aperture parallel to the longitudinal axis of the implanted stem 101 can be greater than the thickness of the outer perimeter edge of the disk structure itself 301, such as at least 10%, 20%, 30%, 40%, 50%, 75%, 100%, or more greater in some embodiments. While the alignment guide is described as a disk 301 in some embodiments herein, the disk 301 encompasses other arcuate and non-arcuate geometries, and can be arcuate such as circular as shown, oval, or take non-arcuate configurations such as square, rectangular, triangular, hexagonal, or other shapes as desired depending on the desired clinical result. In some embodiments, the alignment guide can have a variable thickness, diameter, and/or other dimension, and have a conical or box-like geometry.

The images illustrate an embodiment where disk 301 and slot 300 make up an integral piece. However, a disk and slot could be made up of multiple pieces. For example, some embodiments might have a disk structure that has interchangeable slots for different sized or shaped implants. The disk and slot structures themselves may be made from plastic, metal (e.g., stainless steel, titanium, shape memory metals, etc.), a polymer, and/or any surgical and/or biocompatible material known in the art. In some embodiments, the alignment guide has a peel-away, perforation, or other feature 302 between the slot 300 and the outer perimeter 303 of the alignment guide 301 to allow for easy removal of the alignment guide after placement of the stem, and can be one-time use in some embodiments. The feature can be, for example, parallel to or coaxial with, or normal to the longitudinal axis of the slot 300.

The images show slot 300 that allows the stem 100 to pass through a channel in a direction approximately at an angle of 90 degrees to a plane containing a bone-facing surface of the disk 301. Disk 301 can also have an edge that is generally perpendicular to the bone cut surface 102. This configuration is advantageous for placing a prosthetic humeral head (illustrated as element 500 in FIG. 5) at a position normal to bone cut surface 102. However, one having ordinary skill in the art should appreciate that this system is adaptable to any configuration desired. For example, disk 301 could be angled to accommodate a prosthetic head 500 that needs to be placed on bone cut surface 102 at an angle. Moreover, the slot 300 could be at an angle other than 90 degrees to accommodate different curves and positioning of the implant, such as about 10, 20, 30, 40, 50, 60, 70, 80 degrees, or ranges involving two or more of the aforementioned angles. In some embodiments, the slot 300 is sized and configured to allow for sliding insertion of the stem along the longitudinal axis of the stem through the alignment guide and into a recess formed in the bone while preventing or substantially preventing rotation of the stem during insertion.

In some embodiments, the surgeon can use slot 300 and disk 301 to install an orthopedic implant, such as a humeral, femoral, or other implant using at least the following steps. After the surgeon has removed the natural humeral head, disk 301 is positioned with slot 300 onto bone cut surface 102. In certain embodiments, slotted disk 301 may be free or fixed to bone cut surface 102 once properly positioned. The procedure for permanently or reversibly fixing slotted disk 301 to bone cut surface 102 might include using adhesives, pins, or any other method known in the art. The prosthetic stem 101 is then guided through the slot 300 for proper alignment into the canal in 104.

The disk structure 301 can be adapted to procedures where prosthetic stem 101 is implanted and then the prosthetic head 500 is attached to the stem using element 100, as well as procedures where prosthetic stem 101 and head 500 are implanted as one unit.

Figure 4A:
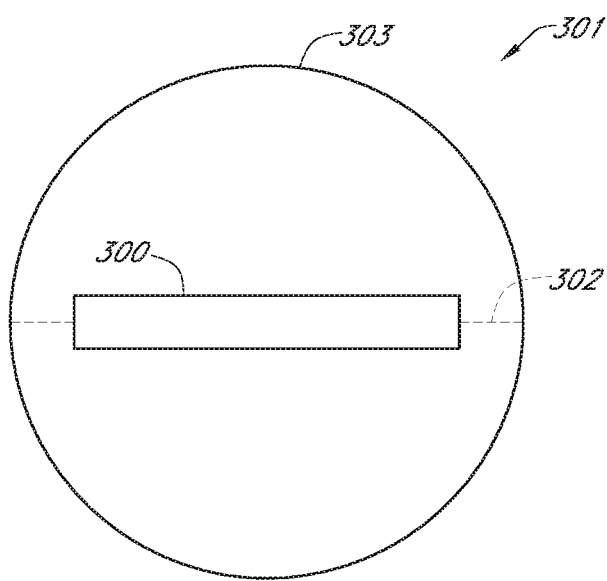
FIGS. 4A-4C illustrate embodiments of alignment guides that can be easily removed from the stem after use.
Figure 4B:
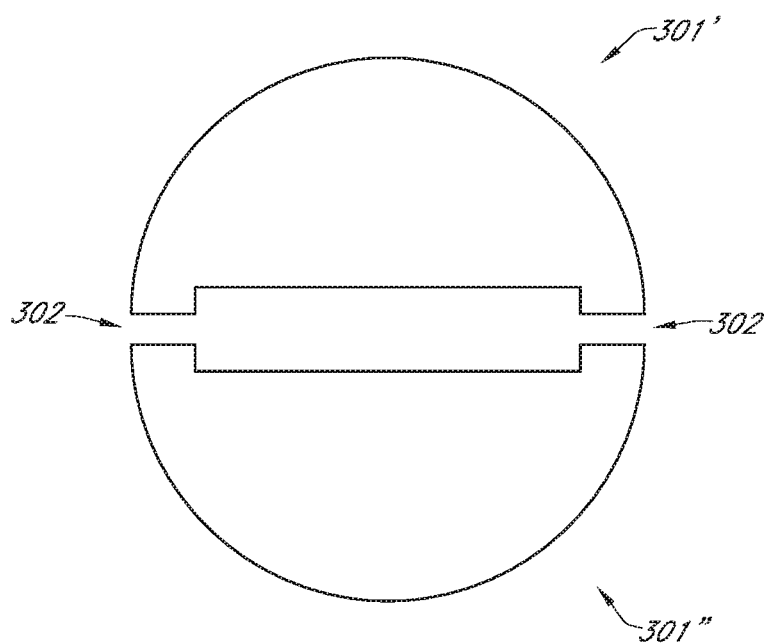
Figure 4C:
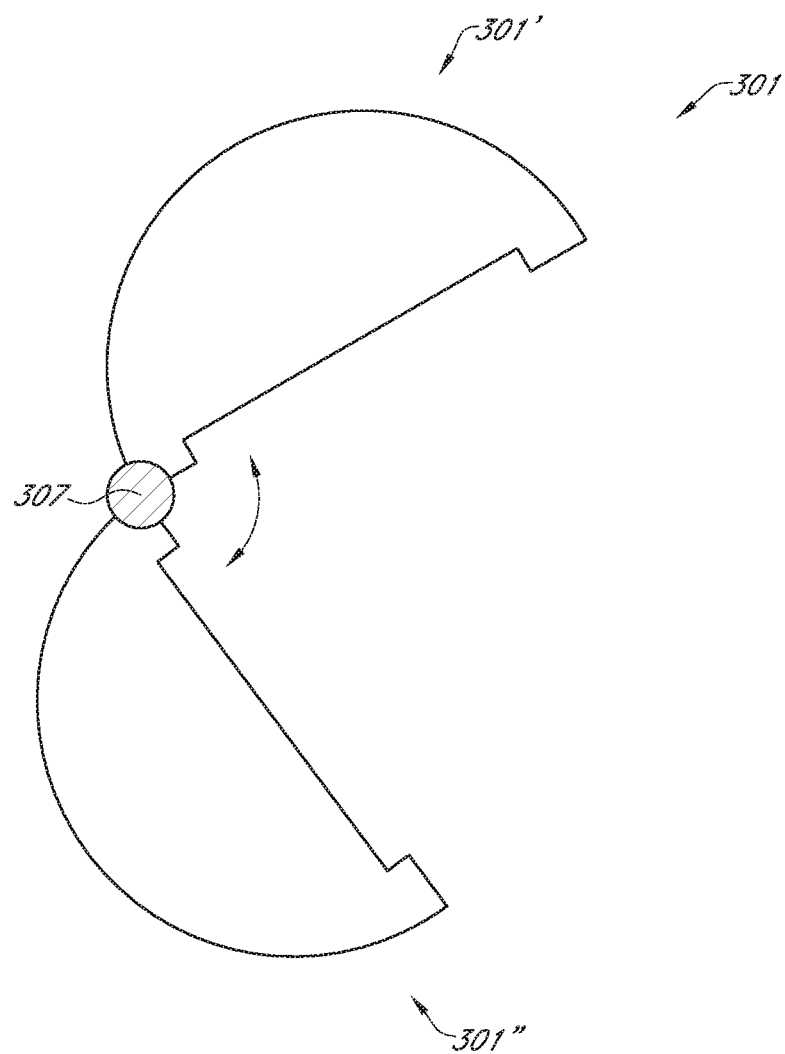

In some embodiments, the alignment guide, e.g., slotted disk structure 301 is configured to be removed prior to the completion of surgery. Some possible advantages of removing the disk include at least the following: disk 301 can be made of less expensive materials that do not necessary have to be biocompatible; a removed disk 301 does not have the possibility of becoming dislodged or misaligned in the patient after surgery; and a removed disk 301 would not add any additional dimensions to the implant. Disk 301 can be removed as the stem 101 is driven down into the canal, or after stem 101 has been placed in the canal. In some embodiments, the disk 301 has a tear-away, frangible, or other portion to create a fracture line between the slot 300 and the outside edge/diameter of the disk 301 that allows the disk 301 to be easily removed and discarded after proper positioning of the stem 101. FIGS. 4A and 4B illustrate an embodiment of an alignment guide 301 with perforated or other areas (dashed line) 302 such that the alignment guide 301 can after use separate into a plurality of separate pieces 301', 301". In some embodiments, the separate pieces 301', 301" are physically separable into discrete halves, or other symmetric or asymmetric sections 301', 301" in other embodiments. FIG. 4C illustrates an embodiment of an alignment guide 301 with a hinge 307 or other movable structure such that the alignment guide 301 can be easily pulled apart in the direction of arrows and removed without necessarily completely separating the plurality of pieces 301', 301". In some embodiments, the disk 301 may be configured to stay in the body as part of the implant, can be partially or completely biodegradable, and/or include one, two, or more therapeutic agents, such as antibiotics or anti-inflammatory agents for example. In some embodiments, alignment guide 301 can be partially or completely radiopaque or otherwise visible under X-ray, ultrasound, or other imaging modalities.

Figure 5:
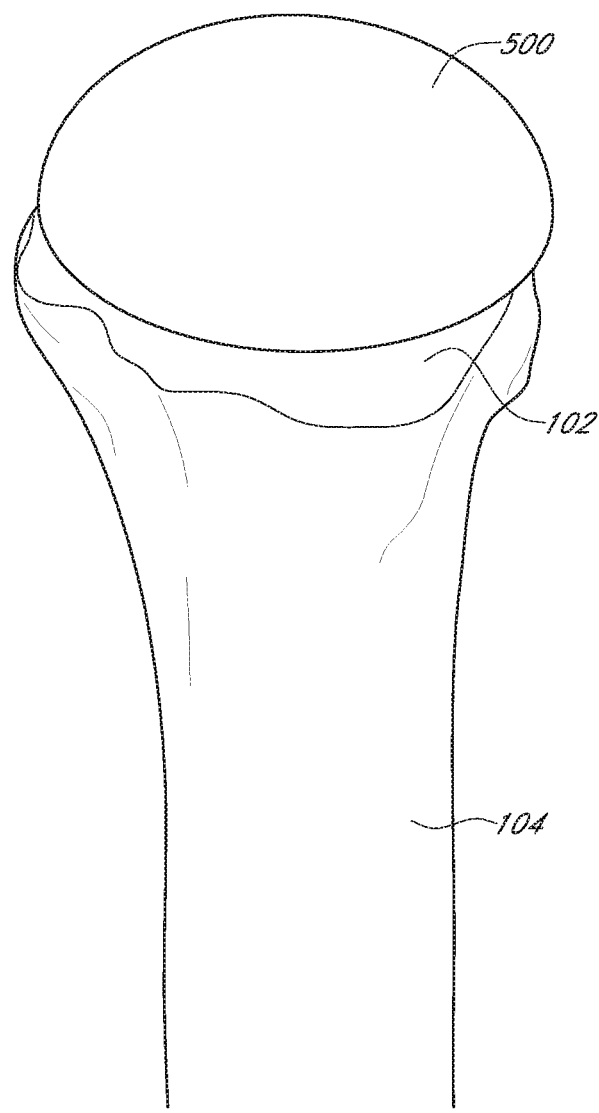
FIG. 5 is an image showing an example of a properly aligned prosthetic humeral implant sitting flush on a bone cut surface.

FIG. 5 shows the result of using an embodiment of the alignment guide 301. The prosthetic head 500 and stem 101 are properly aligned. In some embodiments, the slotted disk structure can be used for guiding a prosthetic stem into a femur. One of ordinary skill in the art would appreciate that the challenges in such a procedure are similar to those for installing a humeral implant. As such, the above embodiments can be modified for use in femoral, or other types of prostheses.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "guiding a stem through an aperture in an alignment guide" includes "instructing the guiding of a stem through an aperture in an alignment guide." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An alignment guide for use with a prosthetic long bone replacement assembly, comprising:

a support having a peripheral edge at an outer circumference of the support, a superior face and an inferior face opposite the superior face, wherein the inferior face is configured to contact and fit on a bone cut surface of a long bone, wherein the peripheral edge of the support has a thickness defined by a distance from the superior face to the inferior face; and an aperture within the support configured to guide a prosthetic stem through the aperture into a canal into an operative site, wherein the prosthetic stem has an axis extending along a length of the prosthetic stem, wherein the aperture is bounded by sidewalls that define the aperture, the sidewalls having a thickness dimension that extends axially superior or inferior beyond the superior or inferior face of the support in a direction of the prosthetic stem axis, wherein the thickness of the sidewalls is greater than the thickness of the peripheral edge of the support; and a movable structure at the peripheral edge at the outer circumference of the support configured to allow the alignment guide to be disassociated from the prosthetic stem.

2. The alignment guide of claim 1, wherein the aperture is defined by a sidewall configured to extend from the support.

3. The alignment guide of claim 1, wherein at least one of the sidewalls is partially curved in order to guide the prosthetic stem into a curve of the canal in a long bone.

4. The alignment guide of claim 1, wherein the support is configured to be stably placed at an angle to the bone cut surface of the long bone such that a prosthetic head of the prosthetic stem is optimally positioned on the long bone surface.

5. The alignment guide of claim 1, wherein the support is configured to be stably placed flush to the bone cut surface of the long bone such that a prosthetic head of the prosthetic stem is optimally positioned on the long bone surface.

6. The alignment guide of claim 1, wherein the support comprises a generally arcuate disc.

7. The alignment guide of claim 1, wherein the support comprises a generally conical configuration.

8. The alignment guide of claim 1, wherein the support comprises a generally box-like configuration.

9. The alignment guide of claim 1, wherein the movable structure comprises a hinge.

10. The alignment guide of claim 1, wherein the dimension of the sidewalls extending axially superior or inferior beyond the length of the peripheral edge of the support is at least 10%, 20%, 30%, 40%, 50%, 75%, or 100% of the length of the peripheral edge of the support.

* * * * *